United States Patent [19]

Chono et al.

[11] Patent Number: 6,139,866
[45] Date of Patent: *Oct. 31, 2000

[54] TAPE FORMULATION FOR PERCUTANEOUS ADMINISTRATION CONTAINING FENTANYI

[75] Inventors: Hideharu Chono; Takaaki Terahara; Tatsuaki Suzuki; Naruhito Higo, all of Tsukuba, Japan

[73] Assignee: Hisamitsu Pharmaceutical Co., Inc., Saga, Japan

[ * ] Notice: This patent is subject to a terminal disclaimer.

[21] Appl. No.: 08/981,475

[22] PCT Filed: May 13, 1997

[86] PCT No.: PCT/JP97/01595

§ 371 Date: Jan. 13, 1998

§ 102(e) Date: Jan. 13, 1998

[87] PCT Pub. No.: WO97/42952

PCT Pub. Date: Nov. 20, 1997

[30] Foreign Application Priority Data

May 13, 1996 [JP] Japan .................................. 8-142210

[51] Int. Cl.$^7$ .............................. A61L 9/70; A61L 15/16; A61L 15/00; A61L 31/38
[52] U.S. Cl. .......................... 424/443; 424/446; 424/448; 424/445; 424/449; 514/352
[58] Field of Search ..................................... 424/443, 445, 424/446, 448, 447, 407; 514/352

[56] References Cited

U.S. PATENT DOCUMENTS

| 5,176,916 | 1/1993 | Yamanaka et al. | 424/448 |
| 5,462,744 | 10/1995 | Gupte et al. | 424/448 |
| 5,484,913 | 1/1996 | Stillwell | 536/57 |

*Primary Examiner*—Theodore J. Criares
*Attorney, Agent, or Firm*—Townsend & Banta

[57] ABSTRACT

A tape formulation for percutaneous administration containing fentanyl which comprises fentanyl or a salt thereof, a pressure sensitive adhesive and sodium acetate, is disclosed. The salt of fentanyl is preferably fentanyl citrate. The tape formulation of the present invention is little irritation to the skin and excellent in the percutaneous permeation of fentanyl and has a high stability even after the passage of time.

13 Claims, No Drawings

TAPE FORMULATION FOR PERCUTANEOUS ADMINISTRATION CONTAINING FENTANYI

This application is a 371 of PCT/JP97/01595 filed May 13, 1997.

TECHNICAL FIELD

The present invention relates to a tape formulation for percutaneous administration containing fentanyl (chemical name: 1-phenethyl-4-N-proplonyl-anilino-piperidine) or a salt thereof, which is very excellent in transdermal permeable property and which has a low irritative property to skins. The tape formulation for percutaneous administration containing fentanyl of the present invention is greatly expected to be utilized as a prolonged-action anesthetic and analgesic.

BACKGROUND ART

Fentanyl, in particular fentanyl citrate is known as a pharmaceutical having a high analgesic effect. However, there was no useful administration method of the pharmaceutical for relatively long lasting pains such as carcinomatous pains, since its elimination half life is short and thus its effects does not last though it is utilized for the constant rate instillation before and after operation.

In the USA, a prolonged-action patch formulation containing fentanyl base (trade name: DURAGESIC) is put on the market. However, it has the disadvantage of being highly irritative to administered regions (The PII value showing a primary irritant index to rabbit skins of the patch formulation is 2.2, which is a very high value compared with that of the formulation of the present invention which is 0.3 to 0.8 (see Table 3).

Further, although the attempts to formulate fentanyl citrate into a tape formulation for percutaneous administration have been made, it could not be used clinically, since the solubility of fentanyl citrate in nonaqueous base is low and thus the transdermal permeable property of the formulation, in which fentanyl is contained in a nonaqueous base, is very low.

Therefore, an object of the present invention is to dissolve the above problems in connection with the prior arts, and to provide a tape formulation for percutaneous administration containing fentanyl, which has a low irritative property to skin, which is extremely excellent in the transdermal permeable property of fentanyl, and which is stable during the storage period.

The present inventors have researched earnestly in order to achieve the above object, and as the results, they found that a tape formulation for percutaneous administration which is extremely excellent in transderaml permeable property and which has a low irritative property to skin, can be prepared, by adding sodium acetate to a pressure sensitive adhesive base containing fentanyl or a salt thereof, and thus completed the present invention.

DISCLOSURE OF INVENTION

Thus the present invention relates to a tape formulation for percutaneous administration containing fentanyl which comprises fentanyl or a salt thereof, a pressure sensitive adhesive and sodium acetate.

The present invention also relates to the tape formulation for percutaneous administration containing fentanyl, which comprises 0.05 to 20%(w/w) of fentanyl or a salt thereof, 0.1 to 98%(w/w) of a pressure sensitive adhesive and 0.01 to 15%(w/w) of sodium acetate.

The present invention also relates to the tape formulation for percutaneous administration containing fentanyl, wherein the salt of fentanyl is fentanyl citrate.

The present invention also relates to the tape formulation for percutaneous administration containing fentanyl, wherein the weight ratio of formulation of fentanyl citrate and sodium acetate is (1 to 5):(0.5 to 2.5).

The present invention also relates to the tape formulation for percutaneous administration containing fentanyl, wherein the weight ratio of formulation of fentanyl citrate and sodium acetate is (3 to 5):(1.5 to 2.5).

The present invention also relates to the tape formulation for percutaneous administration containing fentanyl, wherein the weight ratio of formulation of fentanyl citrate and sodium acetate is 2:1.

The present invention also relates to the tape formulation for percutaneous administration containing fentanyl, which further comprises an oil and/or a tackifier.

The present invention also relates to the tape formulation for percutaneous administration containing fentanyl, which further comprises a transdermal absorption enhancer.

The present invention also relates to the tape formulation for percutaneous administration containing fentanyl, wherein the pressure sensitive adhesive comprises two components of polyisobutylene and styrene-isoprene-styrene block copolymer.

BEST MODE FOR CARRYING OUT THE INVENTION

The tape formulation for percutaneous administration containing fentanyl of the present invention will be explained in detail, hereinafter.

The pharmacological active component of the tape formulation for percutaneous administration containing fentanyl of the present invention, is fentanyl itself or a salt thereof. The salt of fentanyl is not particularly limited, and an inorganic salt and an organic salt thereof may be used. As typical fentanyl salts, citrate, hydrochloride, fumarate and the like may be exemplified. Among them, fentanyl citrate is particularly preferable. The fentanyl or a salt thereof may be used alone, and a mixture of at least two of them may be used.

The fentanyl or a salt thereof is preferably contained in an amount ranging from 0.05 to 20%(w/w) based on the total amount of the adhesive layer of the tape formulation for percutaneous administration of the present invention. If the amount of fentanyl or a salt thereof is less than 0.05 %(w/w), a sufficient permeation amount can not be obtained as a tape formulation for percutaneous administration, and if the amount exceeds 20%(w/w), it exerts a bad influence on the physical properties of the formulation itself and thus it is not preferable.

The pressure sensitive adhesive contained in the adhesive layer of the tape formulation for percutaneous administration containing fentanyl of the present invention, is not limited, but polyisobutylene (PIB), styrene-isoprene-styrene block copolymer (SIS) [e.g., Califlex D-1111, Califlex Tr-1107 manufactured by Shell Chemical; JSR5000, JSR-5002, SR5100 manufactured by Japan Synthetic Rubber Co., Ltd.; Quintack 3421 manufactured by Nippon Zeon Co., Ltd.], isoprene rubber, styrene-butadiene-styrene copolymer (SBS) [e.g., Califlex TR-1101 manufactured by Shell Chemical], acrylic polymer [e.g., a copolymer comprising at least two components selected from the group comprising 2-ethylhexyl acrylate, vinyl acetate, ethyl acrylate, methacrylate, methoxyethyl acrylate and acrylic acid, such as PE-300 (manufactured by Nippon Carbide Industries Co., Inc.,)] may be exemplified as preferable examples. These polymers may be used alone or a mixture of at least two of them may be used. Among them, two components comprising PIB and SIS is preferably used. In this case, the weight ratio of formulation of PIB and SIS is preferably 1:1 to 1:4.

The pressure sensitive adhesive is preferably contained in an amount ranging from 0.1 to 98%(w/w), more preferably from 0.1 to 70%(w/w), most preferably from 0.1 to 50%(w/w), based on the total amount of the adhesive layer of the tape formulation for percutaneous administration of the present invention. If the amount of the pressure sensitive adhesive is less than 0.1%(w/w), the physical properties of the formulation itself will be poor and thus it is not preferable. If the amount exceeds 98%(w/w), a satisfactory adhesive property to human skin can not be obtained and it is not preferable.

The transdermal permeable property of fentanyl or a salt thereof is highly increased by formulating sodium acetate in the adhesive layer of the tape formulation for percutaneous administration containing fentanyl of the present invention. The sodium acetate is preferably contained in an amount ranging from 0.01 to 15%(w/w), more prefabaly from 0.01 to 10 %(w/w), most prefably from 0.01 to 5%(w/w), based on the total amount of the adhesive layer. If the amount of sodium acetate is less than 0.01%(w/w), the effect of remarkably improving the transdermal permeable property can not be obtained. If the amount exceeds 15%(w/w), the irritativeness to skin is increased, thus it is not preferable.

If the fentanyl salt is fentanyl citrate, the maximum effects may be obtained in the respects of the physical property and transdermal permeable property when the weight ratio of formulation of fentanyl citrate and sodium acetate is (1 to 5):(0.5 to 2.5), preferably (3 to 5):(1.5 to 2.5), more preferably 2:1. The amount of sodium acetate is less than the ratio of formulation, the transdermal permeable property of the drug is decreased suddenly, and the amount of sodium acetate exceeds the ratio of formulation, the tape formulation will be inhomogeneous and the physical properties such as adhesive property will be poor and thus it is not preferable.

In addition, a tackifier may be formulated in the adhesive layer of the formlation of the present invention so as to impart an adhesive property to the formulation since the adhesive property of the pressure sensitive adhesive is low. As preferable examples of the tackifiers, polyterpene resins, petroleum resins, rosins, rosin esters, oil-soluble phenol resins and the like may be exemplified. As the concrete examples of the tackifiers, Clearon P-105, Foral 105, Arcon P-100, KE-311, KE-100, Super Ester S-100, Tamanol 521, YS Resin 75, KR-610 and the like may be exemplified by trade names.

The tackifiers is preferably contained in the range from 0.1 to 70%(w/w), more preferably from 5 to 50%(w/w), and most preferably from 10 to 35%(w/w), based on the total amount of the adhesive layer of the formulation of the present invention.

Further, an oil may be formulated in the adhesive layer as a softening agent in order to improve the processability and to control the adhesive property of the tape formulation for percutaneous administration of the present invention. As the oil, for example, liquid paraffin, squalane, olive oil, Tsubaki oil, Persic oil and peanut oil are preferable, and liquid paraffin is most preferable.

The oil is preferably contained in an amount ranging from 1 to 70%(w/w), more preferably from 10 to 60%(w/w), and most prefably from 20 to 50%(w/w), based on the total amount of the adhesive layer of the formulation of the present invention.

Further, a transdermal absorption enhancer may be formulated in the adhesive layer of the formulation of the present invention depending on the necessities. As the transdermal absorption enhancer, any compounds an absorption enhancing effect in skins of which is recognized, may be used. For example, fatty acids having carbon chains of 6 to 20, aliphatic alcohols, fatty acid esters or ethers, aromatic organic acids, aromatic alcohols, aromatic organic acid esters or ethers may be exemplified. In addition, lactic acid esters, acetic acid esters, monoterpene compounds, sesquiterpene compounds, Azone or its derivatives, glycerin fatty acid esters, sorbitan fatty esters, polysorbates, polyethylene glycol fatty acid esters, polyoxyethylene hardened castor oils, sucrose fatty acid esters and the like may be exemplified. As the concrete examples of the enhancer, caprylic acid, capric acid, caproic acid, lauric acid, myristic acid, palmitic acid, stearic acid, oleic acid, linolic acid, linolenic acid, lauryl alcohol, myristyl alcohol, oleyl alcohol, cetyl alcohol, methyl laurate, isopropyl myristate, myristyl myristate, octyldodecyl myristate, cetyl palmitate, salicylic acid, methyl salicylate, ethylene glycol salicylate, cinnamic acid, methyl cinnamate, cresol, cetyl lactate, ethyl acetate, propyl acetate, geraniol, thymol, eugenol, terpineol, l-menthol, borneol, d-limonene, isoeugenol, isoborneol, nerol, dl-camphor, glycerol monolaurate, glycerol monooleate, sorbitan monolaurate, sucrose monolaurate, polysorbate 20, polyethylene glycol monolaurate, polyethylene glycol monostearate, HCO-60 (hardened castor oil), 1-[2-(decyl thio)ethyl] azacyclopentane-2-one (hereinafter it abbreviated as "pirotiodecane") are preferable, and lauryl alcohol, myristyl alcohol, ethylene glycol salicylate and pirotiodecane are most preferable.

These transdermal absorption enhancers is preferably contained in an amount ranging from 0.01 to 20%(w/w), more preferably in an amount ranging from 0.1 to 10%(w/w), most preferably in an amount ranging from 0.5 to 5%(w/w), based on the total amount of the adhesive layer of the tape of the present invention. If the amount of the transdermal absorption enhancer exceeds 20%(w/w), the irritations to skin such as erythema and edema are shown, and if the amount is less than 0.01%(w/w), the effect of formulating the transdermal absorption enhancer can not be obtained, and thus it is not preferable.

In addition, a hydrophilic polymer may be contained in the tape formulation of the present invention depending on the necessities in order to absorb the aqueous components such as sweat produced from skins. As the hydrophilic polymer, for example, light silicic anhydride, cellulose derivatives [carboxymethylcellulose (CMC), sodium carboxymethylcellulose (CMCNa), methylcellulose (MC), hydroxypropyl methylcellulose (HPMC), hydroxypropyl cellulose (HPC), hydroxyethyl cellulose (HEC)], starch derivatives (Pullulan), polyvinyl alcohol (PVA), polyvinyl pyrrolidone (PVP), vinyl acetate (VA), carboxyvinyl polymer (CVP), ethyl vinyl acetate (EVA), Eudragit, gelatin, polyacrylic acid, sodium polyacrylate, polyisobutylene maleic anhydride copolymer, alginic acid, sodium alginate, carrageenan, gum arabi, tragacanth, gum karaya, and polyvinyl methacrylate are preferable, and light silicic anhydride, cellulose derivatives (CMCNa, HPMC, HPC, MC) and Eudragit are more preferable.

The hydrophilic polymer is preferably contained in an amount ranging from 0.1 to 20%(w/w), more preferably 0.5 to 10%(w/w), based on the total amount of the adhesive layer of the tape formulation for percutaneous administration of the present invention.

In addition, a cross-linking agent, a preservative, an antioxidant and another components may be formulated in the adhesive layer of the formulation of the present invention.

As the cross-linking agent, a thermosetting resin such as an amino resin, a phenol resin, an epoxy resin, an alkid resin, an unsaturated polyester, an isocyanate compound, a block isocyanate compound, an organic cross-linking agent, and an inorganic corss-linking agent such as a metal or a metal compound are preferable. As the preservative, ethyl p-oxy benzoate, propyl p-oxy benzoate, butyl p-oxy benzoate and the like are preferable. As the antioxidant, tocopherol and its ester derivatives, ascorbic acid, stearic acid ester, nordihydroguaiaretic acid, dibutyl hydroxytoluene (BHT), butyl hydroxy anisol (BHA) and the like are preferable.

The adhesive layer of the tape formulation of the present invention preferably comprises a nonaqueous base, and the effects of the present invention may be obtained effectively by making the base nonaqueous.

The adhesive layer comprising the above comonents may be prepared by any conventional methods. For example, when the layer is prepared by a solvent method, the formulation of the present invention may be prepared by adding other components other than polymers to an organic solvent solution of the polymers, then stirring, and applying the mixture on a backing film and drying. When the polymers to be formulated can be applied by a hot-melt method, the formulation of the present invention may be obtained by dissolving the polymer components at a high temperature, then adding another components, stirring, and applying on a backing film.

The tape formulation of the present invention may comprise any layers provided that it has an adhesive layer having the above components, and another layers and components of the layers are not limited. For example, the tape formulation for percutaneous administration may comprise, besides the adhesive layer, a backing layer supporting the adhesive layer, a releasable liner layer provided on the adhesive layer, and the like.

The backing layer may comprise, for example, fabric, non-woven fabric, polyurethane, polyvinyl acetate, polyvinylidene chloride, polyethylene, polyethylene terephthalate, polybutylene terephthalate, paper, aluminum sheet and the like, and a composite material thereof.

The tape formulation for percutaneous administration of the present invention is a very useful means for mitigating pains for the patients who can not take orally a anesthetic analgesic easily, since fentanyl or a salt thereof is absorbed continuously via skins by the tape formulation of the present invention. In addition, the tape formulation of the present invention can be administered non-invasively and thus can decrease the burdens of the patients compared with the continuous intradermal aministration method being an invasive method. Further, as to the dose can be controlled easily, e.g., by cutting the formulation, depending on the conditions, ages, body weights, sex distinctions and another factors of patients.

EXAMPLES

The present invention will be explained in more detail with the following Examples, hereinafter. However, the present invention is not be limited to the Examples, and the present invention extends to all such modifications and variations as will be apparent to those skilled in the art without departing the scope of the present invention. In the Examples, all "%" are %(w/w) unless noted.

Example 1

| | |
|---|---|
| Sodium acetate | 2.5% |
| Acrylic polymer (PE-300) | 88.5% |
| Toluene diisocyanate | 1.0% |
| Pirotiodecane | 3.0% |
| Fentanyl citrate | 5.0% |
| Total Amount | 100% |

Sodium acetate, pirotiodecane and fentanyl citrate were added to ethanol, and stirred to dissolve them at room temperature. Then, a solution of acrylic polymer in ethyl acetate and toluene diisocyanate were added to the mixture and stirred. The mixture was applied onto a polyethylene terephthalate film (PET) (30 μm), and it was cross-linked thermally at 90° C. for 15 minutes so as to have an adhesive layer of 50 μm. Using the adhesive layer, a tape formulation for percutaneous administration of the present invention was prepared by a conventional method.

Example 2

| | |
|---|---|
| Sodium acetate | 1.5% |
| Pirotiodecane | 3.0% |
| Liquid paraffin | 38.0% |
| Polyterpene resin tackifier | 29.5% |
| Polyisobutylene | 7.5% |
| Styrene-isoprene-Styrene block copolymer | 16.5% |
| Antioxidant (BHT) | 0.5% |
| Aluminum silicate | 0.5% |
| Fentanyl citrate | 3.0% |
| Total Amount | 100% |

After the components except sodium acetate, pirotiodecane and fentanyl citrate were dissolved and mixed at 180° C., the rest components were added and dispersed so as to have a homogeneous mixture. Then the mixture was applied onto a PET film (30 μm) to have an adhesive layer of 100 μm. Using the adhesive layer, a tape formulation for percutaneous administration of the present invention was prepared by a conventional method.

Example 3

| | |
|---|---|
| Sodium acetate | 2.5% |
| Pirotiodecane | 3.0% |
| Liquid paraffin | 39.5% |
| Polyterpene resin tackifier | 21.7% |
| Polyisobutylene | 6.8% |
| Styrene-isoprene-styrene block copolymer | 20.4% |
| Antioxidant (BHT) | 0.5% |
| Aluminum silicate | 0.6% |
| Fentanyl citrate | 5.0% |
| Total Amount | 100% |

After the components except sodium acetate, pirotiodecane and fentanyl citrate were dissolved and mixed at 180° C., the rest components were added and dispersed so as to have a homogeneous mixture. Then the mixture was applied onto a PET film (30 μm) to have an adhesive layer of 100 μm. Using the adhesive layer, a tape formulation for percutaneous administration of the present invention was prepared by a conventional method.

Example 4

| Sodium acetate | 2.5% |
| Liquid paraffin | 12.5% |
| Oil-soluble phenol resin tackifier | 39.5% |
| Polyisobutylene | 7.5% |
| Styrene-isoprene-styrene block copolymer | 30.5% |
| Antioxidant (BHT) | 0.5% |
| Lauryl alcohol | 2.0% |
| Fentanyl citrate | 5.0% |
| Total Amount | 100% |

After the components except lauryl alcohol, sodium acetate and fentanyl citrate were dissolved and mixed at 180° C., the rest components were added and dispersed so as to have a homogeneous mixture. Then the mixture was applied onto a PET film (30 μm) to have an adhesive layer of 100 μm. Then using the adhesive layer, a tape formulation for percutaneous administration of the present invention was prepared by a conventional method.

Example 5

| Sodium acetate | 1.5% |
| Crotamiton | 3.0% |
| Liquid paraffin | 38.5% |
| Polyterpene resin tackifier | 29.5% |
| Polyisobutylene | 7.5% |
| Styrene-isoprene-styrene block copolymer | 16.5% |
| Antioxidant (BHT) | 0.5% |
| Fentanyl citrate | 3.0% |
| Total Amount | 100% |

After stirring to dissolve sodium acetate, crotamiton, fentanyl citrate and liquid paraffin at 80° C., the mixture was mixed with a cyclohexane solution in which styrene-isoprene-styrene block copolymer, polyisobutylene, polyterpene resin tackifier and antioxidant had been dissolved previously. Then the mixture was applied onto a PET film (30 μm), and dried at 85° C. for 30 minutes so as to have an adhesive layer of 50 μm. Using the adhesive layer, a tape formulation for percutaneous administration of the present invention was prepared by a conventional method.

Example 6

| Sodium acetate | 2.5% |
| Liquid paraffin | 35.0% |
| Polyterpene resin tackifier | 25.5% |
| Polyisobutylene | 7.0% |
| Styrene-isoprene-styrene block copolymer | 24.0% |
| Antioxidant (BHT) | 0.5% |
| Aluminum silicate | 0.5% |
| Fentanyl | 5.0% |
| Total Amount | 100% |

After the components except sodium acetate and fentanyl were dissolved and mixed at 180° C., the rest components were added and dispersed so as to have a homogeneous mixture. Then the mixture was applied onto a PET film (30 μm) to have an adhesive layer of 100 μm. Using the adhesive layer, a tape formulation for percutaneous administration of the present invention was prepared by a conventional method.

Example 7

| Sodium acetate | 0.5% |
| Pirotiodecane | 3.0% |
| Liquid paraffin | 29.0% |
| Polyterpene resin tackifier | 42.1% |
| Polyisobutylene | 7.0% |
| Styrene-isoprene-styrene block copolymer | 16.4% |
| Antioxidant (BHT) | 0.5% |
| Aluminum silicate | 0.5% |
| Fentanyl citrate | 1.0% |
| Total Amount | 100% |

Using the above components (Fentanyl citrate:Sodium acetate=2:1), a tape formulation for percutaneous administration of the present invention was prepared by the method as described in Example 2.

Example 8

| Sodium acetate | 1.5% |
| Pirotiodecane | 3.0% |
| Liquid paraffin | 28.9% |
| Polyterpene resin tackifier | 41.5% |
| Polyisobutylene | 6.9% |
| Styrene-isoprene-styrene block copolymer | 16.2% |
| Antioxidant (BHT) | 0.5% |
| Aluminum silicate | 0.5% |
| Fentanyl citrate | 1.0% |
| Total Amount | 100% |

Using the above components (Fentanyl citrate:Sodium acetate=2:3), a tape formulation for percutaneous administration of the present invention was prepared by the method as described in Example 2.

Example 9

| Sodium acetate | 2.5% |
| Pirotiodecane | 3.0% |
| Liquid paraffin | 28.7% |
| Polyterpene resin tackifier | 41.0% |
| Polyisobutylene | 6.8% |
| Styrene-isoprene-styrene block copolymer | 16.0% |
| Antioxidant (BHT) | 0.5% |
| Aluminum silicate | 0.5% |
| Fentanyl citrate | 1.0% |
| Total Amount | 100% |

Using the above components (Fentanyl citrate:Sodium acetate=2:5), a tape formulation for percutaneous administration of the present invention was prepared by the method as described in Example 2.

Example 10

| | |
|---|---|
| Sodium acetate | 0.5% |
| Pirotiodecane | 3.0% |
| Liquid paraffin | 28.7% |
| Polyterpene resin tackifier | 41.0% |
| Polyisobutylene | 6.8% |
| Styrene-isoprene-styrene block copolymer | 16.0% |
| Antioxidant (BHT) | 0.5% |
| Aluminum silicate | 0.5% |
| Fentanyl citrate | 3.0% |
| Total Amount | 100% |

Using the above components (Fentanyl citrate:Sodium acetate=6:1), a tape formulation for percutaneous administration of the present invention was prepared by the method as described in Example 2.

Example 11

| | |
|---|---|
| Sodium acetate | 1.5% |
| Pirotiodecane | 3.0% |
| Liquid paraffin | 28.5% |
| Polyterpene resin tackifier | 40.5% |
| Polyisobutylene | 6.8% |
| Styrene-isoprene-styrene block copolymer | 15.7% |
| Antioxidant (BHT) | 0.5% |
| Aluminum silicate | 0.5% |
| Fentanyl citrate | 3.0% |
| Total Amount | 100% |

Using the above components (Fentanyl citrate:Sodium acetate=2:1), a tape formulation for percutaneous administration of the present invention was prepared by the method as described in Example 2.

Example 12

| | |
|---|---|
| Sodium acetate | 2.5% |
| Pirotiodecane | 3.0% |
| Liquid paraffin | 28.2% |
| Polyterpene resin tackifier | 40.0% |
| Polyisobutylene | 6.7% |
| Styrene-isoprene-styrene block copolymer | 15.6% |
| Antioxidant (BHT) | 0.5% |
| Aluminum silicate | 0.5% |
| Fentanyl citrate | 3.0% |
| Total Amount | 100% |

Using the above components (Fentanyl citrate:Sodium acetate=6:5), a tape formulation for percutaneous administration of the present invention was prepared by the method as described in Example 2.

Example 13

| | |
|---|---|
| Sodium acetate | 0.5% |
| Pirotiodecane | 3.0% |
| Liquid paraffin | 28.2% |
| Polyterpene resin tackifier | 40.0% |
| Polyisobutylene | 6.7% |
| Styrene-isoprene-styrene block copolymer | 15.6% |
| Antioxidant (BHT) | 0.5% |
| Aluminum silicate | 0.5% |
| Fentanyl citrate | 5.0% |
| Total Amount | 100% |

Using the above components (Fentanyl citrate:Sodium acetate=10:1), a tape formulation for percutaneous administration of the present invention was prepared by the method as described in Example 2.

Example 14

| | |
|---|---|
| Sodium acetate | 1.5% |
| Pirotiodecane | 3.0% |
| Liquid paraffin | 28.2% |
| Polyterpene resin tackifier | 39.5% |
| Polyisobutylene | 6.5% |
| Styrene-isoprene-styrene block copolymer | 15.3% |
| Antioxidant (BHT) | 0.5% |
| Aluminum silicate | 0.5% |
| Fentanyl citrate | 5.0% |
| Total Amount | 100% |

Using the above components (Fentanyl citrate:Sodium acetate=10:3), a tape formulation for percutaneous administration of the present invention was prepared by the method as described in Example 2.

Example 15

| | |
|---|---|
| Sodium acetate | 2.5% |
| Pirotiodecane | 3.0% |
| Liquid paraffin | 28.0% |
| Polyterpene resin tackifier | 38.9% |
| Polyisobutylene | 6.5% |
| Styrene-isoprene-styrene block copolymer | 15.1% |
| Antioxidant (BHT) | |
| Aluminum silicate | 0.5% |
| Fentanyl citrate | 5.0% |
| Total Amount | 100% |

Using the above components (Fentanyl citrate:Sodium acetate=2:1), a tape formulation for percutaneous administration of the present invention was prepared by the method as described in Example 2.

Comparative Examples 1 to 5

Comparative Examples 1 to 5 are each corresponding to Examples 1 to 5, respectively. In each Comparative Example, a tape formulation for percutaneous administration was prepared by the method as described in the corresponding Example, provided that sodium acetate which was used in Examples 1 to 5, was not formulated.

Test Example 1
(In vitro transdermal permeation test)

As to each of the formulations for percutaneous administration obtained in Examples 1 to 5, 7 to 15 and Comparative Examples 1 to 5, the evaluations were made by an in vitro transdermal permeation test using hairless mouse skins.

After picking out the skin of the back region of hairless mouse (6 to 9 weeks old), fats in the dermal side were removed carefully. The skin was installed in a flow-through cell, in which water at 37° C. was circulated around the outer periphery of the receptor layer, so that the dermal side is to be a receptor layer. Each of the tape formulations for percutaneous administration obtained in Examples 1 to 5, 7 to 15 and Comparative Examples 1 to 5 was applied onto the stratum corneum side, and samplings were made at every one hour for 24 hours at a rate of 5 ml/hour using physiological saline to the receptor layer. Then, the flow rates at every one hour were determined accurately, and the drug concentrations were determined by a high-performance liquid chromatography method. The permeation rates at one hour were calculated according to the following formula, and the permeation rates in steady state were determined. The results are shown in Table 1.

Transdermal Permeation Rate $(\mu g/cm^2/hr)$=[Drug concentration $(\mu g/ml)\times$Flow Rate (ml)]/Applied surface area of the formulation $(cm^2)$

TABLE 1

|  | Transdermal Permeation Rate $(\mu g/cm^2/hr)$ |
|---|---|
| Example 1 | 15.5 |
| Example 2 | 25.3 |
| Example 3 | 36.8 |
| Example 4 | 35.2 |
| Example 5 | 22.3 |
| Example 7 | 8.8 |
| Example 8 | 8.2 |
| Example 9 | 7.6 |
| Example 10 | 9.4 |
| Example 11 | 22.2 |
| Example 12 | 20.5 |
| Example 13 | 12.2 |
| Example 14 | 29.4 |
| Example 15 | 35.8 |
| Comparative Example 1 | 1.2 |
| Comparative Example 2 | 1.0 |
| Comparative Example 3 | 1.2 |
| Comparative Example 4 | 1.5 |
| Comparative Example 5 | 1.1 |

As it is clear from Table 2, the tape formulations for percutaneous administration obtained in Examples 1 to 5 and 7 to 15 have higher transdermal permeation rates, compared with the tape formulations for percutaneous administration obtained in Comparative Examples 1 to 5.

In particular, it is proved that the tape formulations for percutaneous administration of Examples 1 to 5, 7, 11, 12, 14 and 15, in which the formulation ratios of fentanyl citrate and sodium acetate are (3 to 5):(1.5 to 2.5), have very high transdermal permeation rates.

Among them, it is proved that the tape formulations for percutaneous administration of Examples 1 to 5, 11 and 15, in which the formulation ratios of fentanyl citrate and sodium acetate are 2:1, have extremely high transdermal permeation rates.

Test Example 2
(Primary irritant to rabbit skin test)

As to each of the tape formulations for percutaneous administration obtained in Examples 1 to 5, the evaluations were made by an in vivo primary irritant test using a rabbit skin.

Each of the tape formulations for percutaneous administration obtained in Examples 1 to 5 was applied onto rabbit skin. The decisions were made in accordance with the criterion of irritativeness to skin shown in Table 2, as to the erythema and edema at 24 and 48 hours after the application. The total of the both scores were regarded as the irritative score at each time. Further, the average value of the irritative scores at each time was regarded as a PII Value. In addition, as the control groups, patch tape of Pharmacopoeia Japonica and a commercially available product in USA (DURAGESIC) were used. The results are shown in Table 3.

TABLE 2

| Criterion of Irritativeness to Skin | | |
|---|---|---|
| Score | Erythema | Edema |
| 0 | None | None |
| 1 | Extremely slight | Extremely slight |
| 2 | Evident | Evident |
| 3 | Middle degree up to intense | Middle degree up to intense |
| 4 | Scarlet, intense | Intense |

TABLE 3

|  | Irritaviness to Skin (PII Value) |
|---|---|
| Example 1 | 0.5 |
| Example 2 | 0.7 |
| Example 3 | 0.5 |
| Example 4 | 0.7 |
| Example 5 | 0.3 |
| Adhesive tape of Pharmacopoeia Japonica | 0.3 |
| DURAGESIC (commercially available in USA) | 2.2* |

*extracts from the application documents to FDA

From the results shown in Table 2, it is proved that the tape formulations for percutaneous administration of Examples 1 to 5 have very low irritative property to skins compared with the conventional product (DURAGESIC), and have the equal irritative property to skins to the patch tape of Pharmacopoeia Japonica which has low irritative property.

Industrial Applicability

With the present invention, fentanyl of a salt thereof can be formulated into a formulation for percutaneous administration which is low-irritative and excellent in transdermal permeable property, which could not be attained by the prior arts.

Thus fentanyl or a salt thereof can be delivered into the body and the pharmacological effects of fentanyl or a salt thereof can be utilized effectively and continuously, by using the tape formulation for percutaneous administration containing fentanyl of the present invention.

Therefore, the tape formulation for percutaneous administration containing fentanyl of the present invention will be a very useful means for mitigating pains for the patients who can not take orally an anesthetic analgesic easily.

What is claimed is:

1. A tape formulation for percutaneous administration containing fentanyl, which comprises fentanyl, citrate and sodium acetate in an adhesive layer which contains a pressure sensitive adhesive containing two components of polyisobutylene and styrene-isoprene-styrene block copolymer and an oil and/or a tackifier, wherein the weight ratio of formulation of fentanyl citrate and sodium acetate is (1 to 5):(0.5 to 2.5).

2. The tape formulation for percutaneous administration containing fentanyl of claim 1, which comprises 0.05 to 20%(w/w) of fentanyl citrate, 0.1 to 98%(w/w) of a pressure sensitive adhesive and 0.01 to 15%(w/w) of sodium acetate.

3. The tape formulation for percutaneous administration containing fentanyl of claim 1, wherein the weight ratio of formulation of fentanyl citrate and sodium acetate is (3 to 5):(1.5 to 2.5).

4. The tape formulation for percutaneous administration containing fentanyl of claim 1, wherein the weight ratio of formulation of fentanyl citrate and sodium acetate is 2:1.

5. The tape formulation for percutaneous administration containing fentanyl of claim 1, which further comprises a transdermal absorption enhancer.

6. The tape formulation for percutaneous administration containing fentanyl of claim 1, which comprises 1 to 70% (w/w) of an oil based on the total weight of the adhesive layer.

7. The tape formulation for percutaneous administration containing fentanyl of claim 1, wherein the oil is selected from the group consisting of liquid paraffin, squalane, olive oil, Tsubaki oil, Persic oil and peanut oil.

8. The tape formulation for percutaneous administration containing fentanyl of claim 1, which comprises 0.1 to 70%(w/w) of a tackifier based on the total weight of the adhesive layer.

9. The tape formulation for percutaneous administration containing fentanyl of claim 1, wherein the tackifier is selected from the group consisting of polyterpene resins, petroleum resins, rosins, rosin esters, oil-soluble and phenol resins.

10. The tape formulation for percutaneous administration containing fentanyl of claim 5, which comprises 0.01 to 20%(w/w) of a transdermal absorption enhancer based on the total weight of the adhesive layer.

11. The tape formulation for percutaneous administration containing fentanyl of claim 1, which further comprises a hydrophilic polymer.

12. The tape formulation for percutaneous administration containing fentanyl of claim 11, which comprises 0.1 to 20%(w/w) of a hydrophilic polymer based on the total weight of the adhesive layer.

13. A tape formulation for percutaneous administration having an adhesive layer, consisting essentially of a pressure-sensitive adhesive, fentanyl citrate and sodium acetate, said fentanyl citrate and sodium acetate being present in a weight ratio of 2:1.

* * * * *

UNITED STATES PATENT AND TRADEMARK OFFICE
CERTIFICATE OF CORRECTION

PATENT NO. : 6,139,866
DATED : October 31, 2000
INVENTOR(S) : Hideharu Chono et al.

It is certified that error appears in the above-identified patent and that said Letters Patent is hereby corrected as shown below:

Column 12,
Line 59, "fentanyl, citrate" should read -- fentanyl citrate --.

Signed and Sealed this

Third Day of May, 2005

JON W. DUDAS
*Director of the United States Patent and Trademark Office*